United States Patent
Malen

(10) Patent No.: US 12,370,080 B2
(45) Date of Patent: Jul. 29, 2025

(54) SYSTEM FOR RECIRCULATING WARM AIR

(71) Applicant: Serengeti Warming Systems, LLC, Temple, GA (US)

(72) Inventor: Andrew Malen, Temple, GA (US)

(73) Assignee: Serengeti Warming Systems, LLC, Temple, GA (US)

( * ) Notice: Subject to any disclaimer, the term of this patent is extended or adjusted under 35 U.S.C. 154(b) by 614 days.

(21) Appl. No.: 17/412,373

(22) Filed: Aug. 26, 2021

(65) Prior Publication Data

US 2023/0063698 A1    Mar. 2, 2023

(51) Int. Cl.
| | | |
|---|---|---|
| A61F 7/00 | (2006.01) | |
| A47C 21/04 | (2006.01) | |
| A47C 27/08 | (2006.01) | |
| A47G 9/02 | (2006.01) | |
| A47G 9/00 | (2006.01) | |

(52) U.S. Cl.
CPC .......... *A61F 7/0097* (2013.01); *A47C 21/048* (2013.01); *A47C 27/081* (2013.01); *A47G 9/0215* (2013.01); *A47G 9/0223* (2013.01); *A47G 2009/003* (2013.01); *A61F 2007/0055* (2013.01); *A61F 2007/0091* (2013.01)

(58) Field of Classification Search
CPC .............. A61F 7/0097; A61F 2007/005; A61F 2007/0091; A47C 21/048; A47C 27/081; A47G 9/0215; A47G 9/0223; A47G 2009/003
See application file for complete search history.

(56) References Cited

U.S. PATENT DOCUMENTS

| | | | |
|---|---|---|---|
| 11,607,337 B1* | 3/2023 | Elghobashi | A61F 7/0085 |
| 12,075,916 B2* | 9/2024 | Newkirk | A61G 7/057 |
| 2002/0094298 A1 | 7/2002 | Monagan | |
| 2003/0200611 A1 | 10/2003 | Chaffee | |
| 2005/0200611 A1* | 9/2005 | Goto | G06F 3/04842 |
| | | | 348/E5.103 |
| 2011/0046704 A1* | 2/2011 | Officier | A61F 7/08 |
| | | | 607/104 |
| 2018/0028770 A1 | 2/2018 | Lewis | |
| 2021/0236978 A1 | 8/2021 | Smith et al. | |
| 2023/0065363 A1 | 3/2023 | Malen | |

OTHER PUBLICATIONS

U.S. Non-Final Office Action dated Sep. 19, 2024 cited in U.S. Appl. No. 17/969,767, 17 pgs.

* cited by examiner

*Primary Examiner* — Nael N Babaa
(74) *Attorney, Agent, or Firm* — BEKIARES ELIEZER LLP

(57) ABSTRACT

A recirculating warm air system configured to connect to an air inflatable product is provided. The system includes a first chamber and a second chamber. The first chamber includes a first air inlet and a first valve located at the first air inlet. The second chamber includes a second valve located between the first chamber and the second chamber, an air outlet, and a first hose connected to the air outlet. The second chamber further includes an air blower and a heater located between the air blower and the air outlet. The second chamber includes a second air inlet, a third valve located at the second air inlet, and a second hose connected to the second air inlet. The first hose and the second hose are configured to connect to the air inflatable product. The system further includes a processing unit configured to control elements of the system.

20 Claims, 4 Drawing Sheets

SYSTEM FOR RECIRCULATING WARM AIR

TECHNICAL FIELD

The present invention relates generally to systems for recirculating warm air and, more particularly, to a recirculating warm air machine and an air inflatable blanket.

BACKGROUND

Thermostabilizing products such as blankets and mattresses are widely used in medicine to keep patients warm. A conventional thermostabilizing blanket is made of porous materials connected to a warm air circulating machine providing warm air to the thermostabilizing blanket through a hose. The thermostabilizing blanket is inflated by the warm air received from the warm air circulating machine.

Because the thermostabilizing blanket is porous, the warm air passes from the inside of the thermostabilizing blanket to the environment. The warm air circulating machine then uses the air from the environment to continue inflating the thermostabilizing blanket. However, the air in the environment can be contaminated during medical procedures. Therefore, the warm air circulating machine may circulate the contaminated air from the environment through the thermostabilizing blanket. Because the same warm air circulating machine with the same hose is usually used for multiple patients, the contaminated air obtained from the room environment of one patient can be released into the room environment of another patient.

Moreover, continuous air flow from the thermostabilizing blanket to an area where a surgery is performed may be problematic, especially when the air exiting the thermostabilizing blanket is contaminated.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to one approach of the present disclosure, a recirculating warm air system is provided. The system may include a first chamber and a second chamber and may be configured to connect to an air inflatable product. The first chamber may include a first air inlet and a first valve located at the first air inlet. The first valve may be configured to pass air into the first chamber. The second chamber may include an air outlet and a first hose connected to the air outlet. The first hose may be configured to connect to the air inflatable product and pass the air to the air inflatable product.

The second chamber may further include an air blower configured to move the air towards the air outlet. The second chamber may include a heater located between the air blower and the air outlet. The second chamber may further include a second air inlet. The second chamber may include a second hose connected to the second air inlet. The second hose may be configured to connect to the air inflatable product and receive the air passing from the air inflatable product. The second chamber may include a second valve located between the first chamber and the second chamber. The second valve may be configured to pass the air from the first chamber to the second chamber. The second chamber may further include a third valve located at the second air inlet. The third valve may be configured to pass the air received from the air inflatable product into the second chamber. The system may further include a processing unit configured to control one or more of the following: the air blower, the heater, the first valve, the second valve, and the third valve.

According to another approach of the present disclosure, a recirculating warm air system is provided. The system may include a recirculating warm air machine and an air inflatable product. The machine may include a first chamber and a second chamber. The first chamber may include a first air inlet and a first valve located at the first air inlet. The first valve may be configured to pass air into the first chamber. The second chamber may include an air outlet and a first hose connected to the air outlet. The first hose may be configured to connect to an air inflatable product and pass the air to the air inflatable product.

The second chamber may further include an air blower configured to move the air towards the air outlet. The second chamber may include a heater located between the air blower and the air outlet. The second chamber may further include a second air inlet. The second chamber may include a second hose connected to the second air inlet. The second hose may be configured to connect to the air inflatable product and receive the air passing from the air inflatable product. The second chamber may further include a second valve located between the first chamber and the second chamber. The second valve may be configured to pass the air from the first chamber to the second chamber. The second chamber may further include a third valve located at the second air inlet. The third valve may be configured to pass the air received from the air inflatable product into the second chamber. The machine may further include a processing unit configured to control one or more of the following: the air blower, the heater, the first valve, the second valve, and the third valve. The air inflatable product may be configured to connect to the second chamber using the first hose and the second hose. The air inflatable product may be made of an air-impermeable material.

Additional objects, advantages, and novel features will be set forth in part in the detailed description section of this disclosure, which follows, and in part will become apparent to those skilled in the art upon examination of this specification and the accompanying drawings or may be learned by production or operation of the example embodiments. The objects and advantages of the concepts may be realized and attained by means of the methodologies, instrumentalities, and combinations particularly pointed out in the appended claims.

BRIEF DESCRIPTION OF THE DRAWINGS

The features of the invention are set forth with particularity in the appended claims. A better understanding of the features and advantages of the present invention will be obtained by reference to the following detailed description that sets forth illustrative embodiments, in which the principles of the invention are utilized, and which the accompanying drawings illustrate.

DETAILED DESCRIPTION

Figure 1:
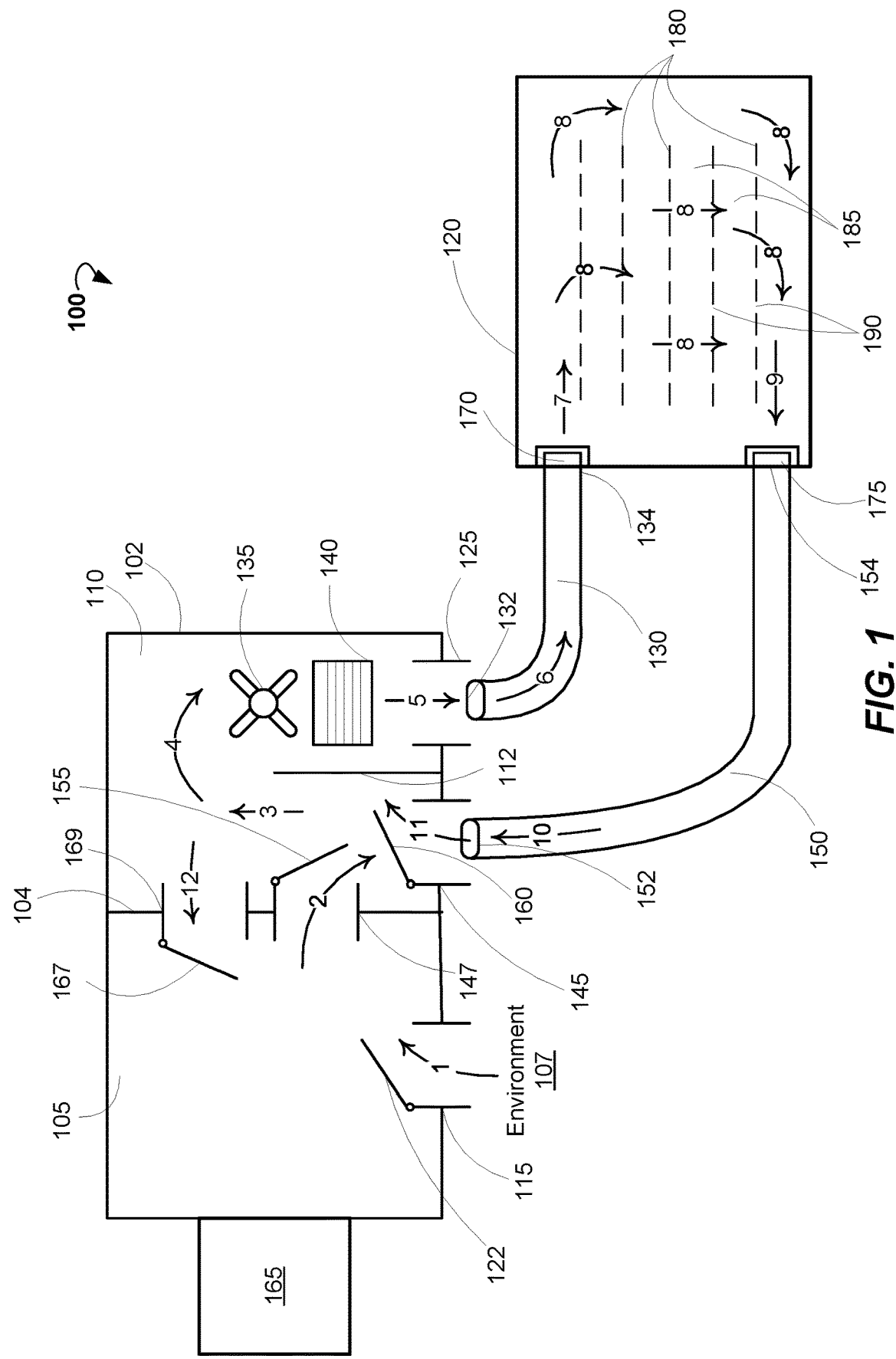
FIG. 1 is a schematic diagram of a recirculating warm air system, according to an example embodiment.

The following detailed description includes references to the accompanying drawings, which form a part of the detailed description. The drawings show illustrations in accordance with exemplary embodiments. These exemplary embodiments, which are also referred to herein as "examples," are described in enough detail to enable those skilled in the art to practice the present subject matter. The embodiments can be combined, other embodiments can be utilized, or structural, logical, and electrical changes can be made without departing from the scope of what is claimed. The following detailed description is, therefore, not to be taken in a limiting sense, and the scope is defined by the appended claims and their equivalents. In this document, the terms "a" and "an" are used, as is common in patent documents, to include one or more than one. In this document, the term "or" is used to refer to a nonexclusive "or," such that "A or B" includes "A but not B," "B but not A," and "A and B," unless otherwise indicated.

The present disclosure is directed to a system for recirculating warm air. The system may include two pieces, namely a recirculating warm air machine and an air inflatable product, such as a blanket or a mattress. The air inflatable product is made of non-porous air-impermeable material. The recirculating warm air machine may be connected to the air inflatable product using two hoses.

The recirculating warm air machine may include two chambers. The first chamber may include a first air inlet and a first valve configured to pass air into the first chamber. The second chamber may include a second valve located between the first chamber and the second chamber. The second valve may pass the air from the first chamber to the second chamber. The second chamber may further include an air outlet, an air blower, and a heater located between the air blower and the air outlet.

When the recirculating warm air machine is turned on, the air blower starts moving the air from the first air inlet to the first chamber to the second valve located between the first chamber and the second chamber. Upon entering the second chamber, the air passes through the air blower and the heater. The heater heats the air passing through the heater. After the air is heated, the air moves to the air outlet in the second chamber, passes through a first hose to the air inflatable product, and inflates the air inflatable product.

When the pressure in the air inflatable product reaches a predetermined threshold, a third valve located in the second chamber opens and the air passes through the second hose from the air inflatable product to the second chamber.

Once the third valve opens, the second valve between the first chamber and the second chamber closes. After the second valve closes, the heated air is recirculated through the air inflatable product and the second chamber.

Thus, the recirculating warm air system recirculates the air in a closed loop without releasing the air into the environment. Accordingly, the air recirculated inside the recirculating warm air system and the air inflatable product does not come in contact with the environment and cannot be contaminated by bacteria residing in the environment.

Moreover, because the air inflatable product is non-porous, no air is released by the air inflatable product into the environment. Therefore, there is no air flowing from the air inflatable product into a surgery area during medical procedures.

Referring now to the drawings, FIG. 1 is a schematic diagram of a recirculating warm air system 100 (also referred to as a system 100), according to an example embodiment. The system 100 may include a recirculating warm air machine 102 configured to connect to an air inflatable product 120. In an example embodiment, the system may include both the recirculating warm air machine 102 and the air inflatable product 120. The recirculating warm air machine 102 may be configured to inflate the air inflatable product 120 with warm air and recirculate the warm air through the air inflatable product 120.

In example embodiments, the air inflatable product 120 may include one of the following: a blanket, a mattress, a bag, a suit, and any other product to be inflated with air. The air inflatable product 120 may be used in medicine to keep patients warm. For example, patients may be laid onto an air inflatable mattress, covered by an air inflatable blanket, laid into an air inflatable bag, or clothed in an air inflatable suit during a medical procedure, such as a medical surgery.

The system 100 may include a first chamber 105 and a second chamber 110 of the recirculating warm air machine 102. The system 100 may further include a chamber separator 104 disposed between the first chamber 105 and the second chamber 110 to separate the first chamber 105 and the second chamber 110 from each other. The chamber separator 104 may include a wall made inside the recirculating warm air machine 102. In some example embodiments, the first chamber 105 and the second chamber 110 may be of the same or different sizes.

The first chamber 105 may include a first air inlet 115 and a first valve 122 located at the first air inlet 115. The first valve 122 may pass air from an environment 107 into the first chamber 105. In an example embodiment, the first air inlet 115 may have the size of about 2-3 inches.

The second chamber 110 may further include a second valve 155 located between the first chamber 105 and the second chamber 110. The second valve 155 may be disposed in an opening 147 made in the chamber separator 104. The second valve 155 may pass the air from the first chamber 105 to the second chamber 110.

The second chamber 110 may have an air outlet 125 and a second air inlet 145. In an example embodiment, the second air inlet 145 and the air outlet 125 may have the size of about 2-3 inches. The second chamber 110 may further include an air blower 135 configured to move the air towards the air outlet 125. The second chamber 110 may have a heater 140 located between the air blower 135 and the air outlet 125.

The second chamber 110 may be attached to a first hose 130 and a second hose 150. The first hose 130 and the second hose 150 may be made of a flexible air-impermeable material, such as plastic or any other applicable material.

The air inflatable product 120 may connect to the second chamber 110 using the first hose 130 and the second hose 150. Specifically, the first hose 130 may connect to the air outlet 125 by a first end 132 of the first hose 130 and may connect to the air inflatable product 120 by a second end 134 of the first hose 130. When connected, the first hose 130 may pass the air from the second chamber 110 to the air inflatable product 120.

The second chamber 110 may further include a second air inlet 145. The second hose 150 may be connected to the second air inlet 145. The second hose 150 may connect to the air inflatable product 120 and receive the air from the air inflatable product 120. Specifically, the second hose 150 may include a first end 152 and a second end 154. The first end 152 may connect to the second air inlet 145 and the second end 154 may connect to the air inflatable product 120. When connected, the second hose 150 may pass the air from the air inflatable product 120 to the second chamber 110.

The second chamber 110 may further include a third valve 160 located at the second air inlet 145. The third valve 160 may be configured to pass the air received from the air inflatable product 120 into the second chamber 110.

The system 100 may further include a processing unit 165. The processing unit 165 may be configured to control an operation of elements of the system 100. Specifically, the processing unit 165 may be configured to control one or more of the air blower 135, the heater 140, the first valve 122, the second valve 155, the third valve 160, and a fourth valve 167.

Figure 2:
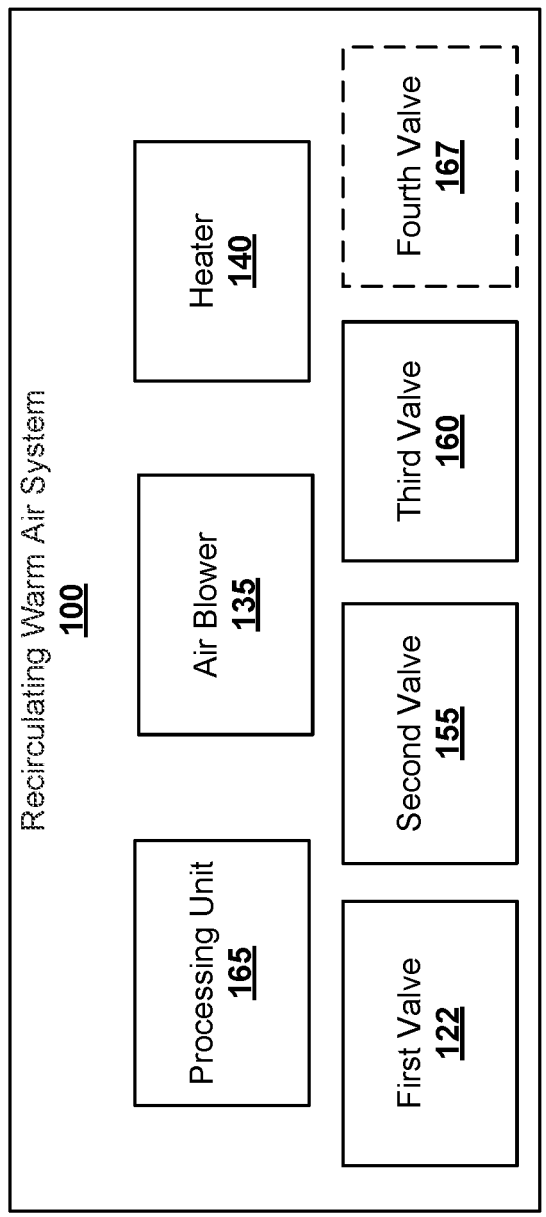
FIG. 2 shows modules of a recirculating warm air system, according to an example embodiment.

FIG. 2 shows modules of the recirculating warm air system 100, according to an example embodiment. The system 100 may include a processing unit 165, an air blower 135, a heater 140, a first valve 122, a second valve 155, a third valve 160, and, optionally, a fourth valve 167. The processing unit 165 may be configured to issue control commands to control the operation of any of the air blower 135, the heater 140, the first valve 122, the second valve 155, the third valve 160, and the fourth valve 167.

Referring again to FIG. 1, upon turning the system 100 on, the processing unit 165 may issue control commands to open the first valve 122 and the second valve 155 and close the third valve 160. Then, the processing unit 165 may issue control commands to turn the air blower 135 and the heater 140 on. Turning the air blower 135 on initiates an intake of the air through the first valve 122 from an environment 107 into the first chamber 105, as shown by arrow 1 in FIG. 1. The air is moved through the second valve 155 from the first chamber 105 to the second chamber 110, as shown by arrow 2.

In the second chamber 110, the air is moved from the second valve 155 to the air blower 135 (as shown by arrow 3) and then through the air blower 135 and the heater 140 (as shown by arrow 4). The heater 140 may be configured to heat the air passing from the air blower 135 to the air outlet 125 to a predetermined temperature. In an example embodiment, the second chamber 110 may further include a guide wall 112. The guide wall 112 may be disposed in the second chamber 110 in order to direct the air from the second valve 155 to the air blower 135.

Upon passing through or in a proximity of the heater 140, the air passes to the air outlet 125 (as shown by arrow 5). Thus, the air is passed from the second chamber 110 to the air inflatable product 120. Specifically, the air is passed from the air outlet 125 of the second chamber 110 to the first hose 130 and then through the first hose 130 (as shown by arrow 6) to the air inflatable product 120. The third valve 160, when closed, prevents the air from exiting the air inflatable product 120. Therefore, as the air blower 135 continues to move the air, the air inflates the air inflatable product 120 (as shown by arrow 7).

The air inflatable product 120 may be made of a flexible non-porous air-impermeable material, such as plastic, rubber, insulated cloth, and so forth. In an example embodiment, the air inflatable product 120 may be in a shape of a parallelepiped with rounded corners and edges. Any other applicable shapes of the air inflatable product 120 can be used for specific purposes.

The air inflatable product 120 may have a first inlet 170 configured to attach to the first hose 130 and a second inlet 175 configured to attach to the second hose 150. The air may pass to the inflatable product 120 through the first inlet 170 (as shown by arrow 7).

The air inflatable product 120 may have one or more dividers 180. The dividers 180 may connect an upper surface and a lower surface of the air inflatable product 120 and divide the air inflatable product 120 into sections 185. The dividers 180 may have air passages 190 for passing the air between sections 185. The air provided into the air inflatable product 120 may inflate the air inflatable product 120 by moving along the sections 185 and through the air passages 190 (as shown by arrow 8).

The processing unit 165 may be configured to determine, based on predetermined criteria, that the amount of the air provided to the air inflatable product has reached a predetermined threshold. For example, the third valve 160 may be set to maintain a predetermined pressure in the air inflatable product 120. Therefore, the third valve 160 may be closed until the pressure in the air inflatable product 120 reaches the predetermined pressure. Reaching the predetermined pressure in the air inflatable product 120 means that the amount of the air provided to the air inflatable product 120 has reached the predetermined threshold. The predetermined pressure maintained by the third valve 160 may be a full inflation pressure of the air inflatable product 120 such that the air inflatable product 120 remains full of warm air.

Upon determining that the amount of the air provided to the air inflatable product 120 has reached the predetermined threshold, the processing unit 165 may close the second valve 155 and open the third valve 160. In other example embodiments, opening of the third valve 160 increases pressure in the second chamber 110, thus closing the second valve 155 between the first chamber 105 and the second chamber 110 and closing the first valve 122 where air enters the recirculating warm air machine 102. Thus, upon closing of the second valve 155 and the opening of the third valve 160, a closed warm air circuit is created in which the air recirculates through the air inflatable product 120 and the second chamber 110. Specifically, the air exits from the second inlet 175 of the air inflatable product 120 (as shown by arrow 9), passes through the second hose 150 (as shown by arrow 10), and enters the second chamber 110 through the second air inlet 145 (as shown by arrow 11). Upon entering the second chamber 110, the air again travels to the air blower 135. The air flow from the air blower 135 and the pressure in the air inflatable product 120 keep the third valve 160 open and keep circulation of the warm air continuous until the system 100 is turned off. Accordingly, the system 100 recirculates the air through the air inflatable product 120 and the second chamber 110 without releasing the air into the environment 107.

In an example embodiment, the system 100 may further include a fourth valve 167 located between the first chamber 105 and the second chamber 110. The fourth valve 167 may be disposed in an opening 169 made in the chamber separator 104. The fourth valve 167 may include a pressure pop-off valve configured to pass the air from the second chamber 110 to the first chamber 105 (as shown by arrow 12), if pressure in the air inflatable product 120 exceeds a predetermined pressure (i.e., if excess pressure is applied to the air inflatable product 120). Upon releasing the air from the second chamber 110 to the first chamber 105, the fourth valve 167 may close again when the pressure returns to the predetermined level in the air inflatable product 120. When the fourth valve 167 opens, the first valve 122 in the first chamber 105 is already closed, thus no air is released from the first chamber 105 into the environment 107.

In an example embodiment, each of the first valve 122, the second valve 155, the third valve 160, and the fourth valve 167 can be one-way valves that allow an air flow to pass in one direction and are completely closed in the opposite direction. Specifically, the first valve 122 may allow the air flow to pass only in the direction from the environment 107 to the first chamber 105. The second valve 155 may allow the air flow to pass only in the direction from the first chamber 105 to the second chamber 110. The third valve 160 may allow the air flow to pass only in the direction from the second hose 150 to the second chamber 110. The fourth valve 167 may allow the air flow to pass only in the direction from the second chamber 110 to the first chamber 105.

In a further example embodiment, the processing unit 165 may be configured to determine that the first hose 130 and the second hose 130 are connected to the second chamber 110. To prevent release of the air from the second chamber 110 into the environment 107, the opening of the first valve 122 may be initiated upon determining that the first hose 130 and the second hose 150 are connected to the second chamber 110. The air outlet 125 and the second air inlet 145 may include sensors to determine whether the first hose 130 is connected to the air outlet 125 and whether the second hose 150 is connected to the second air inlet 145. Thus, the system 100 has a built-in safety feature where the first hose 130 and the second hose 150 must be connected for the recirculating warm air machine 102 to turn on, thus forbidding the recirculating warm air machine 102 to free the air into the environment 107 instead of the air inflatable product 120.

Figure 3A:
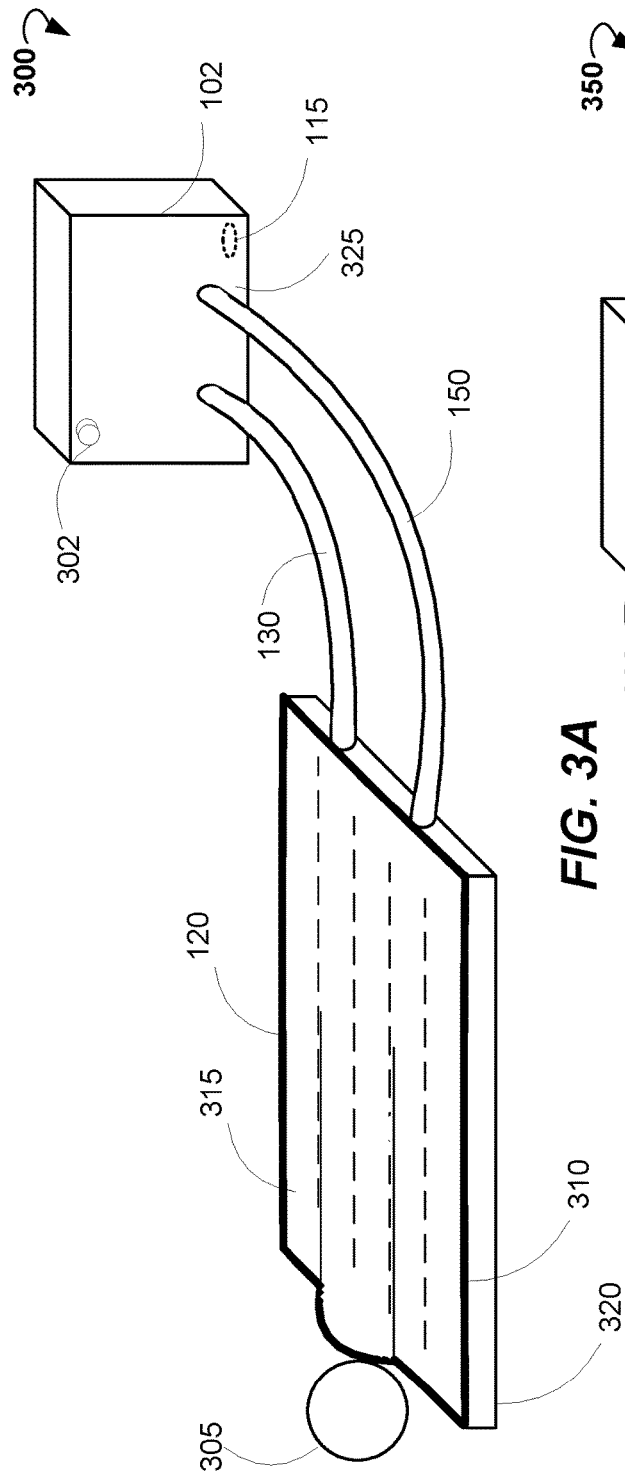
FIGS. 3A and 3B show schematic diagrams of using air inflatable products with a recirculating warm air machine, according to an example embodiment.
Figure 3B:
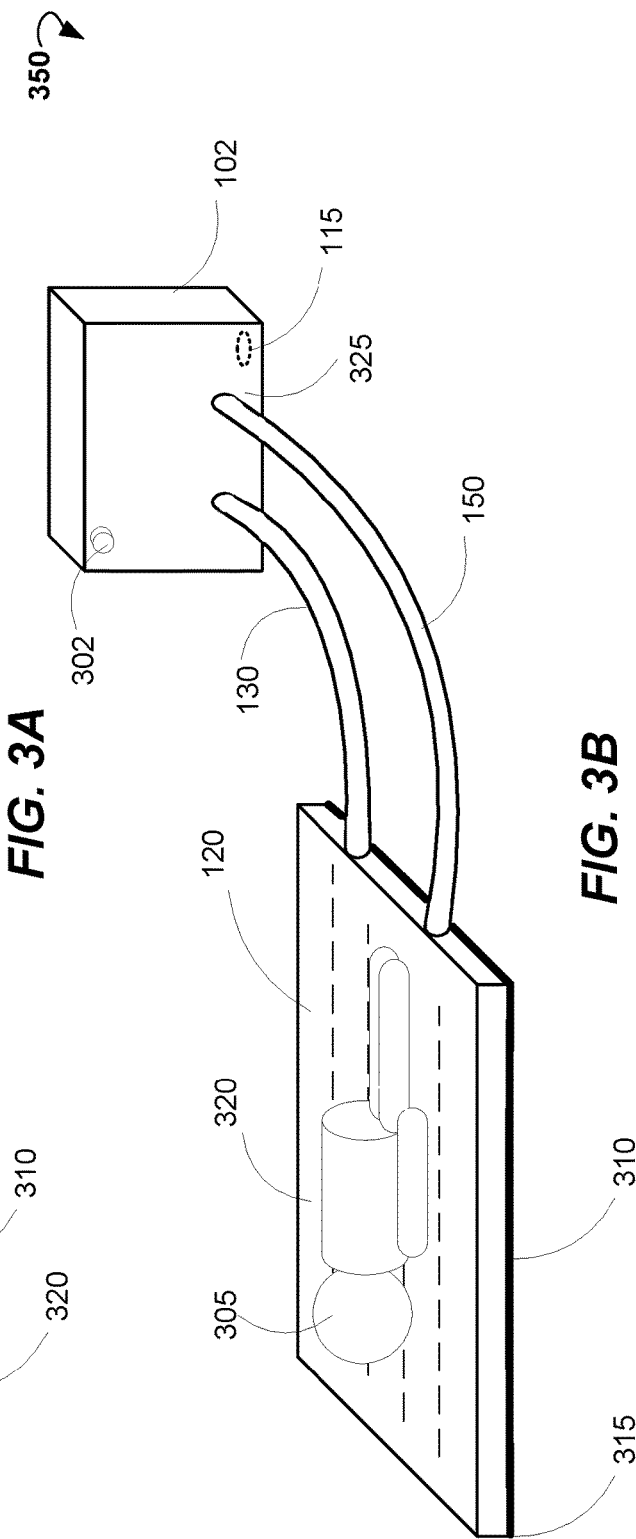

FIGS. 3A and 3B show schematic diagrams 300 and 350, respectively, of using air inflatable products with a recirculating warm air machine, according to an example embodiment. The recirculating warm air machine 102 may have an on/off switch 302 to switch the recirculating warm air machine 102 on and off. The air inflatable product 120 may be connected to the recirculating warm air machine 102 using a first hose 130 and a second hose 150. The first air inlet 115 may be located on a bottom 325 of the recirculating warm air machine 102.

FIG. 3A shows an example embodiment, in which the air inflatable product 120 is a blanket. A patient 305 may be covered with the air inflatable product 120. The recirculating warm air machine 102 may recirculate the warm air through the air inflatable product 120 to keep the patient 305 warm.

In an example embodiment, the air inflatable product 120 may include a heat reflective backing 310. Specifically, the air inflatable product 120 may have a first surface 315 and a second surface 320. The second surface 320 may be intended to face the patient 305. The heat reflective backing 310 may be applied to the first surface 315 and configured to reflect the heat from an inner side of the first surface 315 down towards the second surface 320. The second surface 320 may not have any heat reflective backing. Therefore, the heat from the second surface 320 may contact the patient 305 through the second surface 320 to keep the patient 305 warm.

FIG. 3B shows an example embodiment, in which the air inflatable product 120 is a mattress. A patient 305 may be laid onto the air inflatable product 120. The recirculating warm air machine 102 may recirculate the warm air through the air inflatable product 120 to keep the patient 305 warm. The air inflatable product 120 may include a heat reflective backing 310. Specifically, the air inflatable product 120 may have a first surface 315 and a second surface 320. The second surface 320 may be intended to face the patient 305. The heat reflective backing 310 may be applied to the first surface 315 and configured to reflect the heat from an inner side of the first surface 315 up towards the second surface 320. The second surface 320 may not have any heat reflective backing. Therefore, the heat from the second surface 320 may contact the patient 305 through the second surface 320 to keep the patient 305 warm.

Figure 4:
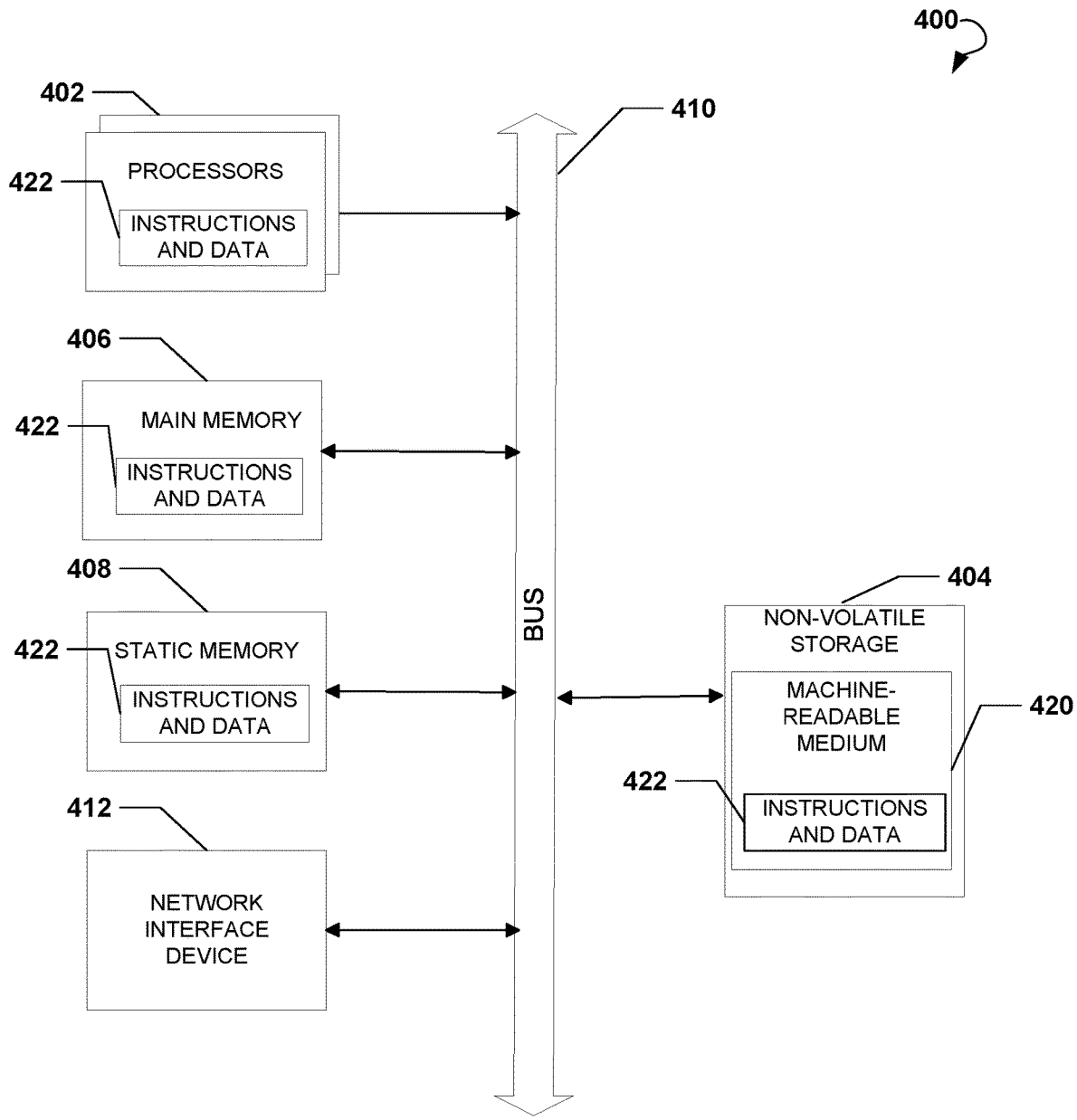
FIG. 4 is a computing system that can be used to implement a recirculating warm air system, according to an example embodiment.

FIG. 4 shows a diagrammatic representation of a computing device for a machine in the exemplary electronic form of a computer system 400, within which a set of instructions for causing the machine to perform any one or more of the methodologies discussed herein can be executed. In various exemplary embodiments, the machine operates as a standalone device or can be connected (e.g., networked) to other machines. In a networked deployment, the machine can operate in the capacity of a server or a client machine in a server-client network environment, or as a peer machine in a peer-to-peer (or distributed) network environment. The machine can be a field programmable gate array, a personal computer (PC), a tablet PC, a set-top box, a cellular telephone, a digital camera, a portable music player (e.g., a portable hard drive audio device, such as an Moving Picture Experts Group Audio Layer 3 (MP3) player), a web appliance, a network router, a switch, a bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The computer system 400 may include a processor or multiple processors 402, a non-volatile storage 404, a main memory 406 and a static memory 408, which communicate with each other via a bus 410. The computer system 400 may also include a network interface device 412. The non-volatile storage 404 may include a machine-readable medium 420, which stores one or more sets of instructions and data 422 embodying or utilized by any one or more of the methodologies or functions described herein. The instructions and data 422 can also reside, completely or at least partially, within the main memory 406 and/or within the processors 402 during execution thereof by the computer system 400. The main memory 406 and the processors 402 also constitute machine-readable media.

While the machine-readable medium 420 is shown in an exemplary embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media. Such media can also include, without limitation, hard disks, floppy disks, NAND or NOR flash memory, digital video disks, Random Access Memory, Read-Only Memory, and the like.

The example embodiments described herein may be implemented in an operating environment comprising software installed on a computer, in hardware, or in a combination of software and hardware.

Thus, recirculating warm air systems have been described. Although embodiments have been described with reference to specific exemplary embodiments, it will be evident that various modifications and changes can be made to these exemplary embodiments without departing from the broader spirit and scope of the present application. Accordingly, the specification and drawings are to be regarded in an illustrative rather than a restrictive sense.

What is claimed is:

1. A recirculating warm air system, the system comprising:
    an air inflatable product having:
        an inflatable body comprising one or more dividers connecting an upper surface of the inflatable body to a lower surface of the inflatable body, and dividing the inflatable body into a plurality of sections, and wherein each divider defines a plurality of air passages distributed along the divider and configured to pass air between the plurality of sections,
        a first hose formed integrally with a first end of the inflatable body, and
        a second hose formed integrally with a second end of the inflatable body; and
    an inflation device comprising:
        a chamber having:
            a first air inlet configured to draw in air from the ambient environment,
            a second air inlet, and
            an air outlet,
        an air blower configured to move air from one or more of the first air inlet or the second air inlet towards the air outlet,
        a heating element disposed between the air blower and the air outlet, the heating element configured to heat the air as it passes in proximity to the heating element, and
        a valve configured to selectively pass air into the chamber from one or more of the first air inlet or the second air inlet, wherein the valve moves between:
            a first state that passes air from the first air inlet and restricts air from the second air inlet, and
            a second state that passes air from both the first air inlet and the second air inlet;
    wherein the first hose is connected to the air outlet and is configured to receive air from the air outlet and pass air to the inflatable body;
    wherein the second hose is connected to the second air inlet and configured to pass air from the inflatable body to the chamber; and
    wherein, responsive to air pressure in the inflatable body reaching a threshold pressure, the valve moves from the first state to the second state.

2. The system of claim 1, wherein the air inflatable product is disposable and configured to be used with only a single patient.

3. The system of claim 1, wherein the threshold pressure within the inflatable body is greater than atmospheric pressure.

4. The system of claim 3, wherein the valve is biased to block the second air inlet until the air pressure in the air inflatable product exceeds the threshold pressure, and wherein the threshold pressure is sufficient to overcome the biasing force of the valve.

5. The system of claim 1, wherein the first air inlet comprises a first one-way valve configured to permit airflow into the chamber and to prevent airflow out of the chamber via the first air inlet.

6. The system of claim 5, wherein the second air inlet comprises a second one-way valve configured to permit airflow into the chamber and to prevent airflow out of the chamber via the second air inlet.

7. The system of claim 1, wherein the one or more dividers comprises a plurality of dividers disposed within the inflatable body in parallel to one another.

8. The system of claim 1, wherein the heating element is configured to heat the air passing from the air blower to the air outlet to a predetermined temperature.

9. The system of claim 1, wherein the chamber is configured to direct the air from the first air inlet and the second air inlet to the air blower.

10. The system of claim 1, wherein the air inflatable product is made of an air-impermeable material.

11. A recirculating warm air system, the system comprising:
    an air inflatable product having:
        an inflatable body comprising one or more dividers connecting an upper surface of the inflatable body to a lower surface of the inflatable body, and dividing the inflatable body into a plurality of sections, and wherein each divider defines a plurality of air passages distributed along the divider and configured to pass air between the plurality of sections,
        a first hose formed integrally with a first end of the inflatable body, and
        a second hose formed integrally with a second end of the inflatable body;
    an inflation device including:
        a chamber having:
            a first air inlet configured to draw in air from the ambient environment,
            a second air inlet, and
            an air outlet configured to provide air to an air inflatable product attached thereto,
        an air blower configured to move air from one or more of the first air inlet or the second air inlet towards the air outlet,
        a heating element disposed between the air blower and the air outlet, the heating element configured to heat the air as it passes in proximity to the heating element, and
        a valve configured to selectively pass air into the chamber from one or more of the first air inlet or the second air inlet, wherein the valve moves between:
            a first state that passes air from the first air inlet and restricts air from the second air inlet, and
            a second state that passes air from both the first air inlet and the second air inlet; and
    a power control unit configured to provide power control for one or more of the air blower or the heating element;
    wherein the first hose is configured to connect to the air outlet and to receive air from the air outlet and pass air to the inflatable body;
    wherein the second hose is configured to connect to the second air inlet and to pass air from the inflatable body to the chamber; and
    wherein the valve restricts airflow from the second air inlet and wherein, responsive to air pressure in the inflatable body reaching a threshold pressure, the valve permits airflow from the second air inlet.

12. The system of claim 11, wherein the first hose is configured to form an airtight connection with the air outlet, and wherein the second hose is configured to form an airtight connection with the second air inlet.

13. The system of claim 11, wherein the air inflatable product is disposable and configured for use with only a single patient, and at least a portion of the air inflatable product is made of an air-impermeable material.

14. The system of claim 11, wherein the air inflatable product is made of an air-impermeable material.

15. The system of claim 11, wherein the one or more dividers comprises a plurality of dividers disposed within the inflatable body in parallel to one another.

16. The system of claim 11, wherein the valve is biased to block the second air inlet until air pressure in the air inflatable product exceeds the threshold pressure, and wherein the threshold pressure is sufficient to overcome the biasing force of the valve.

17. The system of claim 11, wherein the power control unit controls power output to the heating element to heat air passing from the air blower to the air outlet to a predetermined temperature.

18. The system of claim 11, wherein the power control unit controls power output to the air blower to maintain a predetermined flow rate of air through the air inflatable product.

19. A recirculating warm air system, the system comprising:
   an air inflatable product having:
      an inflatable body comprising one or more dividers connecting an upper surface of the inflatable body to a lower surface of the inflatable body, and dividing the inflatable body into a plurality of sections, and wherein each divider defines a plurality of air passages distributed along the divider and configured to pass air between the plurality of sections,
      a first hose formed integrally with a first end of the inflatable body, and
      a second hose formed integrally with a second end of the inflatable body; and
   an inflation device including:
      a chamber having:
         a first air inlet configured to draw in air from the ambient environment,
         a second air inlet, and
         an air outlet configured to provide air to an air inflatable product attached thereto,
      an air blower configured to move air from one or more of the first air inlet or the second air inlet towards the air outlet,
      a heating element disposed between the air blower and the air outlet, the heating element configured to heat the air as it passes in proximity to the heating element to a predetermined temperature, and
      a valve configured to selectively pass air into the chamber from one or more of the first air inlet or the second air inlet, wherein the valve moves between:
         a first state that passes air from the first air inlet and restricts air from the second air inlet, and
      a second state that passes air from both the first air inlet and the second air inlet;
   wherein the first hose is configured to connect to the air outlet and to receive air from the air outlet and pass air to the inflatable body;
   wherein the second hose is configured to connect to the second air inlet and to pass air from the inflatable body to the chamber; and
   wherein, responsive to air pressure in the inflatable body reaching the threshold pressure, the valve is configured to permit airflow from the second air inlet.

20. The system of claim 19, wherein the air inflatable product is disposable and configured for use with only a single patient, and at least a portion of the air inflatable product is made of an air-impermeable material.

* * * * *